(12) United States Patent
Voix et al.

(10) Patent No.: US 8,254,587 B2
(45) Date of Patent: *Aug. 28, 2012

(54) METHOD AND APPARATUS FOR OBJECTIVE ASSESSMENT OF IN-EAR DEVICE ACOUSTICAL PERFORMANCE

(75) Inventors: Jeremie Voix, Montreal (CA); Frederic Laville, Montreal (CA)

(73) Assignee: 3M Innovative Properties Company, St. Paul, MN (US)

( * ) Notice: Subject to any disclaimer, the term of this patent is extended or adjusted under 35 U.S.C. 154(b) by 193 days.

This patent is subject to a terminal disclaimer.

(21) Appl. No.: 12/685,773

(22) Filed: Jan. 12, 2010

(65) Prior Publication Data

US 2010/0111316 A1    May 6, 2010

Related U.S. Application Data

(62) Division of application No. 11/002,081, filed on Dec. 3, 2004, now Pat. No. 7,688,983.

(60) Provisional application No. 60/526,968, filed on Dec. 5, 2003.

(51) Int. Cl.
*H04R 29/00* (2006.01)
*A61B 7/02* (2006.01)
*G01H 3/10* (2006.01)

(52) U.S. Cl. ............... 381/56; 381/58; 181/135; 73/646

(58) Field of Classification Search .................... 381/56, 381/58, 60, 71.5, 72; 181/130, 135, 207; 324/616, 602; 73/645, 646, 585
See application file for complete search history.

(56) References Cited

U.S. PATENT DOCUMENTS

| | | | |
|---|---|---|---|
| 4,060,701 | A | 11/1977 | Epley |
| 4,809,708 | A | 3/1989 | Geisler et al. |
| 5,044,373 | A | 9/1991 | Northeved et al. |
| 5,317,273 | A | 5/1994 | Hanson et al. |
| RE34,961 | E | 6/1995 | Widin et al. |
| 5,577,511 | A | 11/1996 | Killion |
| 5,757,930 | A | 5/1998 | Seidemann et al. |
| 5,923,764 | A | 7/1999 | Shennib |

(Continued)

OTHER PUBLICATIONS

Bockstael, Annelies, *Verifying the Attenuation of Earplugs In Situ: Method Validation on Human Subjects Incluidng Individualized Numerical Simulations*, J. Acoust. Soc. Am., vol. 125, Issue 3, pp. 1479-1489 (Mar. 2009).

*Primary Examiner* — Jesse Elbin (57) ABSTRACT

A method and apparatus for objectively assessing acoustical performance of an in-ear device having a passageway extending there through use a dual microphone probe that removably engages the passageway. The acoustical performance of the in-ear device is performed with the in-ear device inserted into the ear canal of the user and a reference sound source. A clip holding the probe in an acoustic near field of the sound source permits real time calibration thereof. The method and apparatus allow on-site and in-situ measurement of a predicted personal attenuation rating of the device, a subject-fit re-insertion test, an acoustic seal test, a rating test, a stability and reliability test, as well as a protection test of the device with an assessment of a filtered predicted exposure level at the ear for a specific noise exposure level. The apparatus may be simply housed along with the sound source for in-field evaluation tests.

20 Claims, 6 Drawing Sheets

U.S. PATENT DOCUMENTS

| | | |
|---|---|---|
| 5,970,795 A | 10/1999 | Seidmann et al. |
| 6,118,877 A | 9/2000 | Lindemann et al. |
| 6,396,930 B1 | 5/2002 | Vaudrey et al. |
| 6,687,377 B2 | 2/2004 | Voix et al. |
| 6,754,359 B1 * | 6/2004 | Svean et al. ............ 381/328 |
| 7,688,983 B2 | 3/2010 | Voix et al. |
| 2002/0076057 A1 | 6/2002 | Voix |
| 2009/0220099 A1 | 9/2009 | Voix et al. |

* cited by examiner

METHOD AND APPARATUS FOR OBJECTIVE ASSESSMENT OF IN-EAR DEVICE ACOUSTICAL PERFORMANCE

CROSS-REFERENCE TO RELATED APPLICATIONS

The present patent application is a divisional of U.S. patent application Ser. No. 11/002,081, filed on Dec. 3, 2004 now U.S. Pat. No. 7,688,983 (now allowed), and claims priority to U.S. Provisional Patent Application No. 60/526,968, filed on Dec. 5, 2003.

FIELD OF THE INVENTION

The present invention relates to in-ear devices and is more particularly concerned with a method and apparatus for objective assessment of in-ear device acoustical performance.

BACKGROUND OF THE INVENTION

The noisy environment in our industrial society is a health hazard to numerous workers as well as to people engaged in recreational activities generating loud noises.

Users often wear earplugs when operating light machinery such as chainsaws or heavy machinery such as paper industry, printing industry, aircraft industry machines, when participating in sporting activities such as shooting, and when attending various spectator events such as automobile races, truck pulls, and rock concerts, and the like.

The art generally refers to different types of earplugs such as "universal fit" type earplugs that are intended to adapt to the contours of any person's ear canal to provide hearing protection; custom-molded earplugs that have advantages in their comfort, more reliable fit and lower long-term costs due to longer usable life; and semi-custom-molded expandable earplugs that are pre-shaped earplugs having the approximate shape of the ear canal of the individual and expanded with a settable compound material injected therein.

All the above specifically refer to earplugs but it is to be understood that it is similarly applicable to any in-ear device, the latter referring to either earplug device (or hearing protection device (HPD)) or hearing aid device (HAD) for which an attenuation level or an amplification performance level is seek respectively.

One important aspect of preventing hearing loss is the accurate determination of protection from noise offered by an HPD. Protection must be sufficient to protect hearing from noise damage, but should not over-attenuate and interfere with communication and warning signal detection.

Current HPD evaluation is done by using a variety of technical evaluations, statistical corrections and estimations.

Real-Ear Attenuation at Threshold (REAT) is a subjective method of determining the attenuation of a hearing protection device by subtracting the open-ear (unprotected) threshold of hearing from the occluded ear threshold (with the hearing protector in place).

The method for determining REAT is similar to the standard hearing test. The subject is tested in the following manner. Specific tones are given and subject responds when the tones are heard. The hearing threshold is determined based on a given number of positive responses at given sound levels. The REAT will therefore represent the value of attenuation of the HPD reported by the tested individual.

Noise Reduction Rating (NRR) is an estimate of hearing protection capability determined by applying a statistical analysis to a series of REAT measurements. It is a single value figure that estimates the minimum noise reduction measurement theoretically obtained by 98% of the individuals in a laboratory setting.

This percentile of 98% is obtained by subtracting, for every octave band, twice the standard deviation from the mean attenuation measurements reported during the REAT test done according to ANSI S3.19. This is what the American National Standard requirests for NRR calculation by the US Environmental Protection Agency (EPA).

The Personal Attenuation Rating (PAR) is a single number value that represents the individual attenuation that each laboratory subject obtained in the REAT test: it is indeed equivalent to a "personal NRR". For example, the thirty PAR values obtained during an ANSI S3.19 test on an expandable type in-ear device as disclosed in U.S. Pat. No. 6,687,377 to Voix et al. granted on Feb. 3, 2004 were recorded.

For this certification test, PAR values range from 18 dB (obtained in one trial) to 34 dB (obtained in two trials). The NRR calculated from this test series, due to the subtraction of two standard deviations, is 15 dB. This is consistent with the very conservative NRR approach of estimating protection for 98% of users, but is virtually useless in determining individual protected values.

Additionally, there is no objective way of measuring an insertion loss (IL) value provided by an in-ear device. The IL estimation described in all standards (ANSI, ISO, CSA, etc.) is subjectively determined by the individual wearing the in-ear device, as better described hereinbelow.

All standards, such as ANSI, ISO, CSA and the like, require an insertion loss (IL) subjective estimation, generally expressed in dB (decibels), of the acoustic seal provided by the in-ear device based on a ratio of REAT values determined at the tympanic membrane, or eardrum, by the individual himself (thereby subjective), with and without the in-ear device.

Examples of assessments of acoustical performance of in-ear devices are found in the following documents:

U.S. Pat. No. 5,970,795 granted to Seidmann et al. on Oct. 26, 1999 for "Apparatus and method for testing attenuation of in-use insert hearing protectors";

U.S. Pat. No. 5,757,930 granted to Seidmann et al. on May 26, 1998 for "Apparatus and method for testing attenuation of in-use insert hearing protectors";

U.S. Pat. No. 5,577,511 granted to Killion on Nov. 26, 1996 for "Occlusion meter and associated method for measuring the occlusion of an occluding object in the ear canal of a subject";

U.S. Pat. No. 5,317,273 granted to Hanson et al. on May 31, 1994 for "Hearing protection device evaluation apparatus"; and U.S. Pat. No. 4,060,701 granted to Epley on Nov. 29, 1977 for "Method for testing acoustical attenuation of hearing protectors".

The last method taught by Epley is another subjective evaluation method and suffers from the same weaknesses as all the other subjective methods, naming:

the subjectivity of the measurements is a great source of uncertainty and also significantly reduces the possibility of repeatability of the measurements.

the subjective estimation of the attenuation is always larger than the objective measurement of the corresponding IL, especially in the low-frequencies; the "Occlusion Effect" tends to increase the physiological noise (PN) present behind the protector by modifying the acoustic radiation impedance seen from the tympanic membrane.

Other ways of measuring acoustical attenuation or acoustic seal of an in-ear device disclose some devices that could measure the pneumatic pressure leakage of an in ear-device to later on predict its acoustical attenuation or the presence of an "acoustic seal". Obviously, this mere static pressure drop measurement is insufficient to reliably predict the acoustic pressure drop, and numerous materials may prove to provide excellent pressure seal and still perfectly have sound pressure transmitted there through. For example, a ping-pong shell molded in the ear could be tightly sealed therein, but will always transmit sound there through.

Accordingly, there is a need for an apparatus and method for objective assessment of in-ear device acoustical performance.

SUMMARY OF THE INVENTION

It is therefore a general object of the present invention to provide a method and apparatus for objective assessment of in-ear device acoustical performance that obviate the above-mentioned disadvantages.

Key aspects and advantages of the present method and apparatus for objective assessment of in-ear device acoustical performance:

- It is personal: it indicates how well the in-ear device works for the individual under test, in real in-field environment conditions (as opposed to laboratory conditions).
- It is objective: it does not require the cooperation of the individual under test, neither it is susceptible to the objectivity of this individual.
- Understanding the performance parameters of the in-ear device for the individual permits attenuation adjustments to match the capabilities of the in-ear device to the actual noise environment of the user to customize the device to the individual for his activity noise environment with proper sound filters and obtain a Filtered Predicted Exposure Level (F-PEL).
- The corresponding software permits real-time in-situ assessment of a Predicted Personal Attenuation Rating (P-PAR) on the field.
- Assessment can include evaluation of the in-ear device in the noise environment of the user either on the field or via audio reproduction thereof. This can be very important where particular octave bands dominate over the noise environment and assessment of the effectiveness of the in-ear device in those octave bands is of interest.
- The process integrates with subject-fit protocols. The test is repeatable, permitting evaluation of the performance of the in-ear device at any time. This can be useful in working with individuals to encourage and ensure proper usage and fitting of the protector, by using either a complex (personal computer-type or the like) or a simple (pocket-type or the like) apparatus.
- Objective in-situ assessment of an acoustic seal of the in-ear device under subject-fit condition, of a rating level of the in-ear device considering the applicable standard and the actual type of the device, of a protection level of the in-ear device considering the applicable standard and the actual noise environment the user is subjected to, and of a simple reliability (stability) check of all tests performed on the in-ear device by assuring the coherence of all measurements.

In accordance with an aspect of the present invention, there is provided a method for assessing in-situ an acoustic seal of an in-ear device using an apparatus having a sound measurement device connected thereto, the in-ear device having a passageway extending therethrough, the passageway being in fluid communication with an ear canal of an ear when the in-ear device is inserted therein, the sound measurement device being removably engageable into the passageway, said method comprises: a) calibrating said sound measurement device by measuring a reference sound level with said sound measurement device when being submitted to a reference sound source and when being located in a close relationship relative thereto; b) measuring a first sound level outside the ear canal with said sound measurement device when submitted to the sound source and when located in a close relationship relative to the in-ear device and outside the ear canal; c) measuring a second sound level inside the ear canal with said sound measurement device when submitted to the sound source and when engaged into and occluding the passageway with the in-ear device inserted inside the ear canal; and d) assessing the acoustic seal of the in-ear device by subtracting said second sound level from said first sound level.

In one embodiment, step a) includes measuring a reference sound level with said sound measurement device when being submitted to a reference sound source and when being in an acoustic near field relative thereto.

In one embodiment, the method further includes: a1) assessing validity of said reference sound level by determining that said reference sound level is within a predetermined sound level amplitude range, if not step a) is repeated.

Typically, step d) includes indicating presence of acoustic seal when attenuation between said first and second sound levels is equal to or larger than a predetermined threshold value within a predetermined frequency range.

In one embodiment, steps b) and c) are simultaneously performed using first and second sound measurement devices, respectively.

Typically, step d) includes: d1) assessing validity of said first and second sound levels by determining coherence between said first and second sound levels, if not steps b) and c) are repeated.

Typically, step d1) includes determining coherence between said first and second sound levels within a predetermined frequency range. Preferably, determining coherence between said first and second sound levels includes determining that said second sound level substantially linearly follows a contour of said first sound level.

Typically, step d) includes indicating presence of acoustic seal when attenuation between said first and second sound levels is equal to or larger than a predetermined threshold value within a predetermined frequency range.

In one embodiment, step d) includes assessing the acoustic seal of the in-ear device by subtracting said second sound level from said first sound level and using a compensation term relating to the in-ear device.

In one embodiment, step a) includes calibrating first and second sound measurement devices by measuring first and second reference sound levels with said first and second sound measurement devices, respectively, when being submitted to a reference sound source and when being located in a close relationship relative thereto; and wherein steps b) and c) are simultaneously performed using said first and second sound measurement devices, respectively.

Typically, step a) includes simultaneously measuring first and second reference sound levels with said first and second sound measurement devices, respectively, when being submitted to a reference sound source and when being in an acoustic near field relative thereto.

Typically, the method further includes: a1) assessing validity of said first and second reference sound levels by determining that said first and second reference sound levels are within a predetermined sound level template range, if not step a) is repeated.

Typically, step a) includes simultaneously measuring first and second reference sound levels with said first and second sound measurement devices, respectively, when being submitted to a reference sound source and when being in an acoustic near field relative thereto, and determining a transfer function between said first and second reference sound levels.

In one embodiment, the method further includes: a1) assessing validity of said first and second reference sound levels by determining that said transfer function is within a predetermined sound level template range, if not step a) is repeated.

Typically, step d) includes assessing the acoustic seal of the in-ear device by subtracting said second sound level from said first sound level and using said transfer function and a compensation term relating to the in-ear device.

In accordance with another aspect of the present invention, there is provided an apparatus for assessing in-situ an acoustic seal of an in-ear device, the in-ear device having a passageway extending therethrough, the passageway being in fluid communication with an ear canal of an ear when the in-ear device is inserted therein, said apparatus comprises: a controller unit operatively connectable to a sound source; a sound measurement device operatively connecting to said controller unit, said sound measurement device being selectively locatable in a close relationship relative to the in-ear device and outside the ear canal for measuring a first sound level outside the ear canal when submitted to the sound source, said sound measurement device being removably engageable into the passageway to selectively occlude the passageway for measuring a second sound level inside the ear canal with the in-ear device inserted therein when submitted to the sound source; and a means for releasably supporting said sound measurement device located in a close relationship relative to the sound source for measuring a reference sound level when being submitted thereto.

In one embodiment, the means for supporting said sound measurement device is a supporting device, preferably a resilient clip, mountable on the sound source, said clip releasably and resiliently holding said sound measurement device.

In one embodiment, the controller unit controls operation of the sound source.

In one embodiment, the controller unit includes the sound source.

In one embodiment, the sound measurement device is a first sound measurement device, said apparatus further including a second sound measurement device operatively connecting to said controller device, said first sound measurement device being selectively locatable in a close relationship relative to the in-ear device and outside the ear canal for measuring the first sound level outside the ear canal when submitted to the sound source, said second sound measurement device being removably engageable into the passageway to selectively occlude the passageway for measuring the second sound level inside the ear canal with the in-ear device inserted therein when submitted to-the sound source. And, the means for releasably supporting said sound measurement device releasably supports said first and second sound measurement devices located in a close relationship relative to the sound source for measuring first and second reference sound levels when being submitted thereto, relatively.

Typically, the first and second sound measurement devices are connected to one another, preferably in a back-to-back relationship relative to one another to form a dual microphone probe.

In one embodiment, the apparatus further includes a user interface unit operatively connecting to said controller unit.

Typically, the controller unit analyzes said first and second reference sound levels and assesses calibration of said first and second sound measurement devices, said controller unit communicating with said user interface unit to indicate to the user proper functioning of said first and second sound measurement devices.

Typically, the controller unit analyzes said first and second sound levels and assesses validity of said first and second sound levels, said controller unit communicating with said user interface unit to indicate to the user proper measurements of said first and second sound levels.

Typically, the controller unit further assesses an acoustic seal of the in-ear device by comparing said first and second sound levels to one another and by using a transfer function determined from said first and second reference sound levels, said controller unit communicating with said user interface unit to indicate to the user proper acoustic seal of the in-ear device inside the ear.

Typically, the controller unit further assesses an acoustic seal by further using a compensation term relating to the in-ear device.

In one embodiment, the controller unit assesses an acoustic seal of the in-ear device by comparing said first and second sound levels to one another, said controller unit further assessing an acoustic seal by further using a compensation term relating to the in-ear device, said controller unit communicating with said user interface unit to indicate to the user proper acoustic seal of the in-ear device inside the ear.

In one embodiment, the user interface unit includes at least one of a keypad, a keyboard, an alpha-numerical display, a speaker, a led-type display, a monitor-type display, a socket-type connection port and a wireless-type connection port.

In accordance with another aspect of the present invention, there is provided a method for assessing an acoustical performance of an in-ear device using an apparatus having a sound measurement device connected thereto, the in-ear device having a passageway extending therethrough for receiving an acoustic damper therein, the acoustic damper having a predetermined acoustic attenuation thereof, the passageway being in fluid communication with an ear canal of an ear when the in-ear device is inserted therein, the sound measurement device being removably engageable into the passageway, said method comprises: a) calculating an acoustical performance of the in-ear device with the acoustical damper inserted in the passageway thereof from a measured blocked acoustic attenuation obtained with the passageway being occluded using a sound measurement device selectively engaged therein and the predetermined damper acoustic attenuation.

In one embodiment, the method further includes, before step a), the step of: measuring a blocked acoustic attenuation of the in-ear device with the passageway being occluded using the sound measurement device selectively and alternately engaged therein and disengaged therefrom.

In one embodiment, the in-ear device is for being worn by a user subjected to an environment with a predetermined noise exposure level, said method further includes: b) calculating a filtered exposure level at an ear of the user would be subjected to when protected by the in-ear device with the acoustic damper inserted in the passageway thereof inside the environment from the calculated acoustical performance and the predetermined sound exposure level.

In one embodiment, the passageway is for receiving one of a plurality of acoustic dampers, each one of the plurality of acoustic dampers having a respective predetermined damper acoustic attenuation thereof, said method includes: a) calculating a respective acoustical performance of the in-ear device with each one of the plurality of acoustic dampers inserted in the passageway thereof from a measured blocked acoustic attenuation obtained with the passageway being occluded using a sound measurement device selectively engaged therein and a corresponding said predetermined damper acoustic attenuations; b) calculating a respective filtered exposure level at an ear of the user would be subjected to when protected by the in-ear device with respective said plurality of the acoustic dampers inserted in the passageway thereof inside the environment from respective said calculated acoustical performances and the predetermined sound exposure level.

Typically, the method further includes: c) selecting one of the plurality of acoustic dampers providing a corresponding filtered exposure level within or closest to a predetermined optimal exposure level range.

In one embodiment, the method further includes, before step a), for obtaining said predetermined damper acoustic attenuation, the steps of: submitting a user wearing the in-ear device with the passageway thereof being occluded to a gradually increasing or decreasing a volume of a sound level of a predetermined frequency range to determine a first sound level threshold value at which the user start or stop hearing the sound; submitting a user wearing the in-ear device with the acoustic damper inserted in the passageway thereof to a gradually increasing or decreasing a volume of a sound level of a predetermined frequency range to determine a second sound level threshold value at which the user start or stop hearing the sound; and calculating the predetermined damper acoustic attenuation from a difference between said first and second sound level threshold values.

Typically, calculating the predetermined damper acoustic attenuation includes calculating the predetermined damper acoustic attenuation from a difference between first and second average sound level thresholds obtained from a statistically significant number of said first and second sound level threshold values, respectively.

In one embodiment, the method further includes, before step a), for obtaining said, predetermined damper acoustic attenuation, the steps of: submitting a user wearing the in-ear device with the passageway thereof being occluded to a gradually increasing or decreasing a frequency of a sound level of a predetermined volume range to determine a first sound level threshold value at which the user stop or start hearing the sound; submitting a user wearing the in-ear device with the acoustic damper inserted in the passageway thereof to a gradually increasing or decreasing a frequency of a sound level of a predetermined volume range to determine a second sound level threshold value at which the user stop or start hearing the sound; and calculating the predetermined damper acoustic attenuation from a difference between said first and second sound level threshold values.

Typically, calculating the predetermined damper acoustic attenuation includes calculating the predetermined damper acoustic attenuation from a difference between first and second average sound level thresholds obtained from a statistically significant number of said first and second sound level threshold values, respectively.

In accordance with another aspect of the present invention, there is provided an apparatus for assessing an acoustical performance of an in-ear device, the in-ear device having a passageway extending therethrough for receiving an acoustic damper therein, the acoustic damper having a predetermined acoustic attenuation thereof, the passageway being in fluid communication with an ear canal of an ear when the in-ear device is inserted therein, said apparatus comprises: a controller unit operatively connectable to a sound source; a user interface unit operatively connecting to said controller unit to allow a user to interface therewith by storing the predetermined acoustic attenuation of the acoustic damper therein; and a sound measurement device operatively connecting to said controller unit, said sound measurement device being selectively locatable in a close relationship relative to the in-ear device and outside the ear canal for measuring a first sound level outside the ear canal when submitted to the sound source, said sound measurement device being removably engageable into the passageway to selectively occlude the passageway for measuring a second sound level inside the ear canal with the in-ear device inserted therein when submitted to the sound source; said controller unit calculating an acoustical performance of the in-ear device with the acoustical damper inserted in the passageway thereof from a blocked acoustic attenuation obtained with said first and second sound levels and the predetermined damper acoustic attenuation.

In one embodiment, the in-ear device is for being worn by a user subjected to an environment with a predetermined noise exposure level storable within said controller unit, said controller unit calculating a filtered exposure level an ear of the user would be subjected to when protected by the in-ear device with the acoustic damper inserted in the passageway thereof inside the environment from the calculated acoustical performance and the predetermined sound exposure level.

In one embodiment, the passageway is for receiving one of a plurality of acoustic dampers, each one of the plurality of acoustic dampers having a respective predetermined damper acoustic attenuation thereof storable within said controller unit, said controller unit calculating a respective acoustical performance of the in-ear device with each one of the plurality of acoustic dampers inserted in the passageway thereof from a measured blocked acoustic attenuation obtained with the passageway being occluded using a sound measurement device selectively engaged therein and a corresponding said predetermined damper acoustic attenuations, said controller unit further calculating a respective filtered exposure level an ear of the user would be subjected to when protected by the in-ear device with respective said plurality of the acoustic dampers inserted in the passageway thereof inside the environment from respective said calculated acoustical performances and the predetermined sound exposure level.

Typically, the controller unit further selects one of the plurality of acoustic dampers providing a corresponding filtered exposure level within or closest to a predetermined optimal protection level range storable therein.

In accordance with another aspect of the present invention, there is provided a method for assessing an acoustical performance of an in-ear device using an apparatus having a sound measurement device connected thereto, the in-ear device having a passageway extending therethrough, the passageway being in fluid communication with an ear canal of an ear when the in-ear device is inserted therein, the sound measurement device being removably engageable into the passageway, said method comprises: a) measuring a first sound level outside the ear canal with said sound measurement device when submitted to the sound source and when located in a close relationship relative to the in-ear device and outside the ear canal; b) measuring a second sound level inside the ear canal with said sound measurement device when submitted to the sound source and when engaged into and occluding the passageway with the in-ear device inserted inside the ear canal after being fitted thereto and before removal therefrom; c) measuring a third sound level inside the ear canal with said sound measurement device when submitted to the sound source and when engaged into and occluding the passageway with the in-ear device inserted inside the ear canal after removal therefrom and reinsertion therein by the wearer thereof; d) assessing a reference acoustic seal of the in-ear device by subtracting said second sound level from said first sound level and an actual acoustic seal of the in-ear device by subtracting said third sound level from said first sound level; and e) assessing a rating of the in-ear device by comparing said actual acoustic seal relative to said reference acoustic seal.

Typically, steps a) and b) are simultaneously performed using first and second sound measurement devices, respectively.

Typically, step e) further includes comparing said obtained rating to a standardized rating value corresponding to a type of the in-ear device.

In one embodiment, step c) includes measuring a third sound level inside the ear canal with said sound measurement device when submitted to the sound source and when engaged into and occluding the passageway with the in-ear device inserted inside the ear canal after removal therefrom and reinsertion therein by the wearer thereof, and measuring a fourth sound level outside the ear canal with said measurement device when submitted to the sound source and when located in a close relationship relative to the in-ear device and outside the ear canal; and wherein step d) includes assessing a reference acoustic seal of the in-ear device by subtracting said second sound level from said first sound level and an actual acoustic seal of the in-ear device by subtracting said third sound level from said fourth sound level.

Typically, step b) includes: b1) assessing validity of said first and second sound levels by determining coherence between said first and second sound levels, if not steps a) and b) are repeated; and step c) includes: c1) assessing validity of said third and fourth sound levels by determining coherence between said third and fourth sound levels, if not step c) is repeated.

Typically, steps b1) and c1) include determining coherence between said first and second sound levels within a predetermined frequency range and between said third and fourth sound levels within said predetermined frequency range, respectively.

Typically, determining coherence between said first and second sound levels includes determining that said second sound level substantially linearly follows a contour of said first sound level, and determining coherence between said third and fourth sound levels includes determining that said third sound level substantially linearly follows a contour of said fourth sound level.

Typically, the method further includes, before step a), the step of: simultaneously measuring first and second reference sound levels with said first and second sound measurement devices, respectively, when being submitted to a reference sound source and when being in an acoustic near field relative thereto, and determining a transfer function between said first and second reference sound levels.

In accordance with another aspect of the present invention, there is provided an apparatus for assessing in-situ an acoustic seal of an in-ear device, the in-ear device having a passageway extending therethrough, the passageway being in fluid communication with an ear canal of an ear when the in-ear device is inserted therein, said apparatus comprises: a controller unit operatively connectable to a sound source; a user interface unit operatively connecting to said controller unit to allow a user to interface therewith by storing the predetermined acoustic attenuation of the acoustic damper therein; and a sound measurement device operatively connecting to said controller unit, said sound measurement device being selectively locatable in a close relationship relative to the in-ear device and outside the ear canal for measuring a first sound level outside the ear canal when submitted to the sound source, said sound measurement device being removably engageable into the passageway to selectively occlude the passageway for measuring, when submitted to the sound source, a second sound level inside the ear canal with the in-ear device inserted therein being fitted thereto and before removal therefrom, and a third sound level inside the ear canal the in-ear device inserted inside the ear canal after removal therefrom and reinsertion therein by the wearer thereof; said controller unit calculating a reference acoustic seal of the in-ear device by subtracting said second sound level from said first sound level, an actual acoustic seal of the in-ear device by subtracting said third sound level from said first sound level, and a rating of the in-ear device by comparing said actual acoustic seal relative to said reference acoustic seal.

Typically, the controller unit indicates presence of acceptable acoustic seal when said actual acoustic seal is within a predetermined range from said reference acoustic seal.

Typically, the controller unit compares said obtained rating to a standardized rating value corresponding to a type of the in-ear device and stored therein.

In one embodiment, the controller unit assesses validity of said first and second sound levels by determining coherence between said first and second sound levels, if not said first and second sound levels are being re-measured; and assesses validity of said third and fourth sound levels by determining coherence between said third and fourth sound levels, if not said third and fourth sound levels are being re-measured.

Typically, the controller unit determines coherence between said first and second sound levels within a predetermined frequency range and between said third and fourth sound levels within said predetermined frequency range, respectively.

Other objects and advantages of the present invention will become apparent from a careful reading of the detailed description provided herein, with appropriate reference to the accompanying drawings.

BRIEF DESCRIPTION OF THE DRAWINGS

Further aspects and advantages of the present invention will become better understood with reference to the description in association with the following Figures, in which similar references used in different Figures denote similar components, wherein.

DETAILED DESCRIPTION OF THE PREFERRED EMBODIMENTS

With reference to the annexed drawings the preferred embodiments of the present invention will be herein described for indicative purpose and by no means as of limitation.

Figure 1:
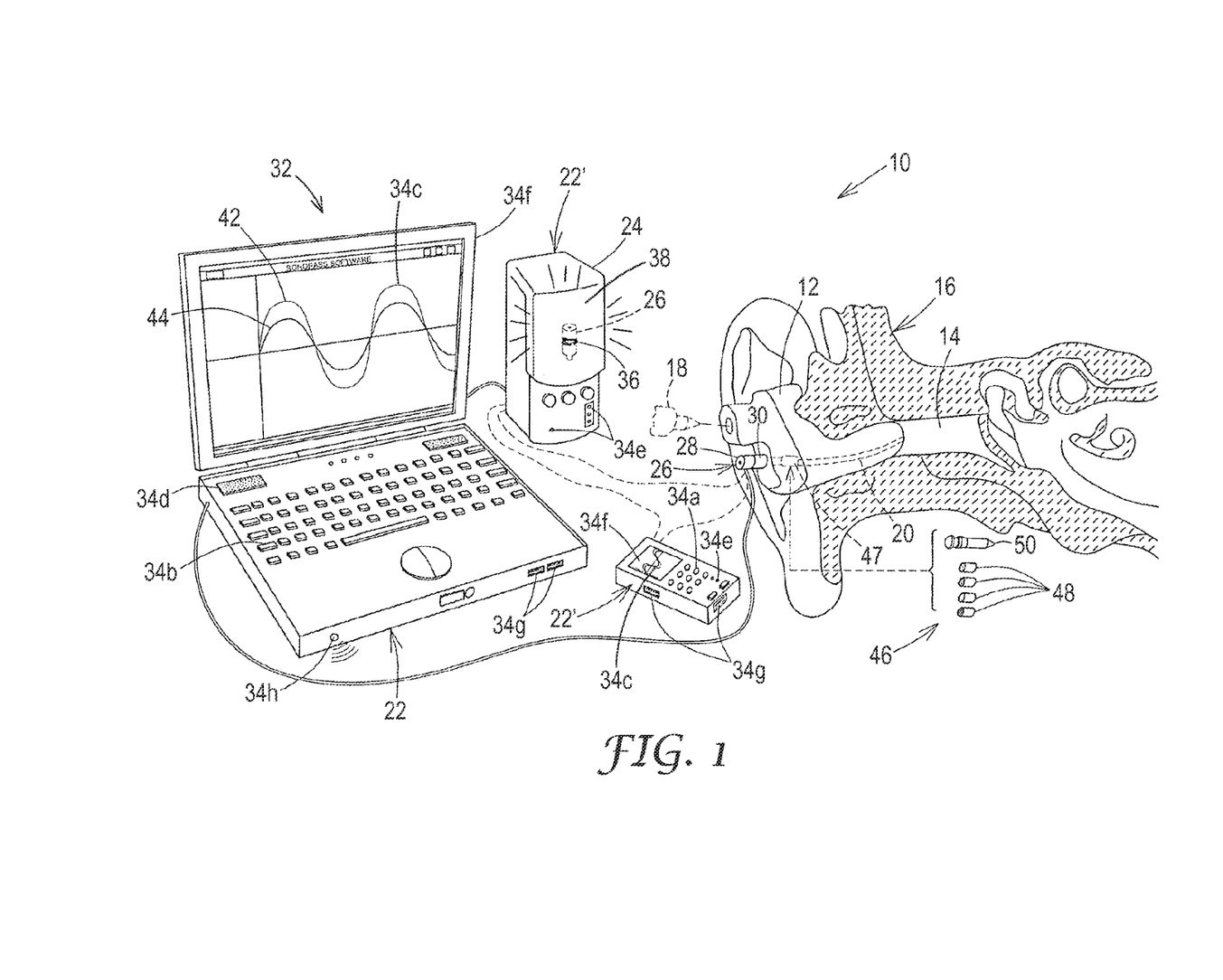
FIG. 1 is a simplified schematic diagram of an apparatus for assessing in-situ an acoustic seal of an in-ear device in accordance with an embodiment of the present invention.

Referring now in more detail to FIG. 1, there is shown an apparatus 10 for assessing in situ acoustical performance of an in-ear device 12 in accordance with an embodiment of the present invention. The in-ear device 12 or earplug, typically made out of generally soft materials such as silicones, acrylic materials and the like, is typically first inserted inside the ear canal 14 of the ear 16 of an individual (user or wearer) and then fitted to the contour thereof using a thermo-settable compound 18 (shown in dotted lines) injected inside the in-ear device 12. The earplug 12 typically includes at least one passageway 20 or sound bore that extends there through to be in fluid communication with the ear canal 14 when the earplug 12 is inserted therein. Although an earplug 12 is being shown throughout the Figures for illustration purposes, one skilled in the art would understand that any type of in-ear device (HPDs, HADs or the like) could be used without departing from the scope of the present invention.

The apparatus 10 typically includes a controller unit 22 operatively connected to a broadband reference sound source 24 to control operation thereof. The sound source 24 provides a sound typically having a frequency range varying from about 100 Hz to about 10000 Hz such that the following preferred octave bands which enclose most audible sounds (including conversation frequency range of about 300 Hz to about 3000 Hz) are essentially covered: 125 Hz, 250 Hz, 500 Hz, 1000 Hz, 2000 Hz, 4000 Hz and 8000 Hz. Typically, the controller 22 is a personal-type computer, a laptop, a palm computer or the like that include a central processing unit (not shown) or the like to process the data and perform assessments. A dual microphone probe 26 that is removably engageable into the passageway 20 of the earplug 12 operatively connects to the controller 22. The probe 26 typically includes first 28 and second 30 sound measurement devices or microphones mounted in a back-to-back relationship relative to one another such that the first microphone 28 measures an external sound pressure level in proximity to the earplug 12 and the second microphone 30 measures an internal sound pressure level inside the ear canal 14 when the earplug 12 is inserted therein, respectively.

Although the used of a dual microphone probe 26 is preferred, one could consider using only one sound measurement device 28 to successively perform all required sound level measurements discussed hereinbelow without departing from the scope of the present invention.

A sound pressure level or sound level refers to a sound of any predetermined frequency and/or amplitude ranges to cover any predetermined amount of octave bands, depending on the application, test and/or apparatus.

A user interface unit 32 is operatively connected to the controller 22 for the user to operate the apparatus 10, provide some inputs and data thereinto and get outputs or data therefrom. The user interface 32 are well known and typically includes at least one of a keypad 34a, a keyboard 34b, an alpha-numerical display 34c, a speaker 34d, a led-type display 34e, a monitor-type display 34f, a socket-type connection port 34g and a wireless-type (Infra-Red (IR), microwaves (MW), voice and the like) connection port 34h and the like for different types of communication protocols.

The controller 22 could also be housed within the same housing as the sound source 24 and interface knobs and led-type display 34e, such that the apparatus 10 could be a "stand-alone" type for in-field assessment of in-ear device acoustical performance.

The apparatus 10 typically includes a means 36 for releasably supporting the probe 26 in a close relationship relative to the sound source 24 for measurements of reference sound pressure levels and/or calibration of the apparatus 10 through proper functioning of the two microphones 28, 30 when being submitted to a reference sound therefrom. The means for supporting the probe 26 is a supporting device such as a resilient clip 36 or the like mounted on the sound source 24, typically in the middle of the speaker grid 38 thereof. Accordingly, the clip 36 releasably supports the probe 26 inside the acoustic near field generated by the sound source 24, as shown in dotted lines in FIG. 1.

As mentioned hereinabove, the Personal Attenuation Rating (PAR) is a single number value that represents the individual attenuation that each laboratory subject obtained in the Real-Ear Attenuation at Threshold (REAT) test: it is indeed equivalent to a "personal Noise Reduction Rating (NRR)".

Determining true PAR for each individual would provide very useful information to determine the hearing protector adequacy and sufficiency. Since it is impossible, even theoretically, to predict PAR from NRR, other objective means to determine PAR were scientifically developed.

The Noise Reduction (NR) is an objective method which is the sound pressure level (SPL) difference measured at the external part of the hearing protection device 12 (HPD) (by an external microphone 28) compared to the SPL measured inside the HPD (by an internal microphone 30).

From an individual measurement of NR, it is possible to predict the corresponding PAR using a "compensation function" which is applied to the NR for every octave band. The "compensation function" addresses transfer function of the outer ear (TFOE), head and torso diffraction of the reference noise source, the length of the microphone probe, the impedance of the occluded ear canal, the resonant frequency of the ear canal, and the like variables. Due to the fact that the compensation function is normally distributed, the predicted REAT will also follow a normalized "Bell Curve".

P-PAR is a global value which confidently represents the PAR. This value is therefore "personal" to the end-user and is extremely useful in assuring the adequate protection needed by this individual rather than a statistically derived value or popular estimate.

It is to be noted that the present invention allows for a real-time monitoring of the inflation of an expandable in-ear device 12 being fitted inside an ear 16 as described in U.S. Pat. No. 6,687,377 granted to Voix et al. on Feb. 3, 2004, although not specifically required.

Also, the present invention is a field method to estimate the noise attenuation obtained by such expandable earplug 12 as worn in the workplace. The proposed method is a MIRE method (Microphone In the Real Ear) that uses the Noise Reduction (NR) measurement on one's earplug to predict, based on a statistical approach, the corresponding subjective attenuation (ATT) that this user would report during a REAT (Real-Ear Attenuation at Threshold) test.

The prediction of an in-ear device attenuation (as reported with REAT method) from on an objective Noise Reduction measurement (MIRE) uses either:
  a statistical approach: A statistical "compensation function" is applied per octave band to estimate the REAT from the NR measured.
  a personal dedicated approach: An analytical "compensation function" is computed from the exact physical and mechanical properties of the subject ear canal as identified using the identification method described hereinafter.

Figure 2:
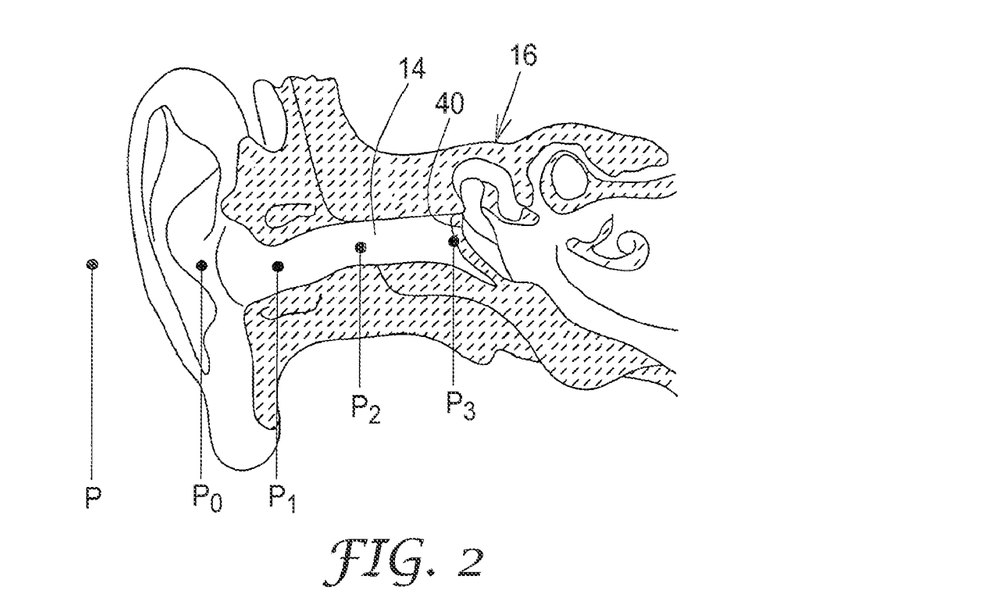
FIGS. 2 and 3 are pictorial representations of the different locations for sound pressure level measurement inside an individual's ear canal without (unoccluded) and with (occluded) an in-ear device, respectively.
Figure 3:
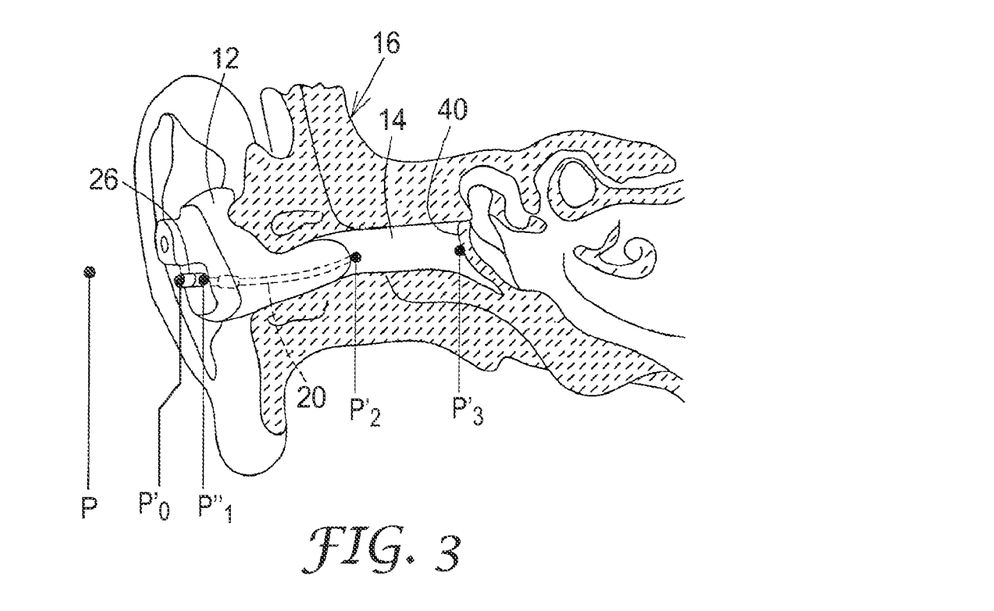

More specifically, and referring to FIGS. 2 and 3, it is known that the IL corresponding to the difference in sound pressure level at eardrum 40 between unoccluded and occluded conditions can be determined by:

$$IL = NR + TFOE$$

where TFOE is the Transfer Function of the Outer Ear, for an unoccluded ear 16 (FIG. 2), and is equal to:

$$TFOE = 20 \log_{10}\left(\frac{P_3}{P}\right)$$

In an occluded ear 16 (FIG. 3), the NR is determined by:

$$NR = 20 \log_{10}\left(\frac{P}{P'_3}\right)$$

It has been clearly demonstrated that the attenuation reported during a REAT measurement may be slightly overestimated (below 500 Hz) due to the masking effect of the physiological noise (PN) on occluded thresholds. It remains that this reported attenuation is a subjective evaluation of the IL and, practically:

$$REAT = IL + PN$$

The measured noise reduction ($NR_M$) measured typically using a dual microphone probe 26 adjacent the in-ear device 12 and measuring the sound pressure levels outside the device 12 being worn by the user and inside the ear canal 14 via the passageway 20 (or sound bore) of the device (see FIG. 1), respectively, is:

$$NR_M = 20 \log_{10}\left(\frac{P'_0}{P''_2}\right)$$

Therefore, combining the previous equations, the measured noise reduction $NR_M$ can be linked to the reported attenuation as follows:

$$REAT = \underbrace{NR_M + TFOE + 20 \log_{10}\left(\frac{P''_2}{P'_2}\right) + 20 \log_{10}\left(\frac{P'_2}{P'_3}\right) + 20 \log_{10}\left(\frac{P}{P'_0}\right) + PN}_{COMP}$$

where:
($P''_2/P'_2$) stands for the "tube effect" of the microphone probe 26;
($P'_2/P'_3$) stands for another "tube effect" of the residual ear canal portion;
($P/P'_0$) stands for the diffraction effect of the subject's head and torso.

A compensation term COMP that contains all the above three corrections, the TFOE and the PN masking effect can be defined. This compensation COMP is subject sensitive and, for a large group, distributes as a standard or normal distribution. Therefore, the simultaneous recording of the $NR_M$ and the REAT for a large number of subjects will determine a global compensation COMP and a corresponding compensation per octave band $COMP^i$ (as identified by the indicia T), respectively. Obviously, the same rationale could be considered by using third of octave bands, twelfth of octave bands or the like without departing from the scope of the present invention.

Knowing the octave band based compensation term $COMP^i$, a corresponding $REAT^i$ can be obtained. Further knowing that the NRR (slightly modified to correspond to selected octave bands) is obtained by:

$$NRR = 10 \log_{10} \sum_i 10^{\frac{100+C_i}{10}} - 10 \log_{10} \sum_i 10^{\frac{100+A^i - \overline{REAT^i} + 2\sigma^i_{REAT}}{10}} - 3$$

where $\overline{REAT^i}$ is a statistical average of REAT;
$C^i$ and $A^i$ are octave band weighting factors, and
$2\sigma^i_{REAT}$ is the two-standard deviation factor showing that a 98% confidence level is considered.

Then the PAR can be derived as follows:

$$PAR = 10 \log_{10} \sum_i 10^{\frac{100+C_i}{10}} - 10 \log_{10} \sum_i 10^{\frac{100+A^i - REAT^i}{10}}$$

Also, the computation of a single number for the rating of a P-PAR using the in-ear device 12, or global personal attenuation rating, is statistically derived from the normalized ($\aleph$) averaged compensation term $\overline{COMP^i}$ and individual noise reduction $NR_{ind}^i$ as being:

$$P\text{-}PAR = \overline{PAR} = NR_{ind}^i + \aleph(\overline{COMP^i}, \sigma_{comp}^i)$$

to give:

$$P - PAR = \overline{PAR}$$
$$= 10 \log_{10} \sum_i 10^{\frac{100+C_i}{10}} - 10 \log_{10} \sum_i 10^{\frac{100+A^i - \overline{\overline{REAT^i}}}{10}}$$

This permits the identification of physical and mechanical properties of one's ear canal from an acoustical measurement.

Figure 4:
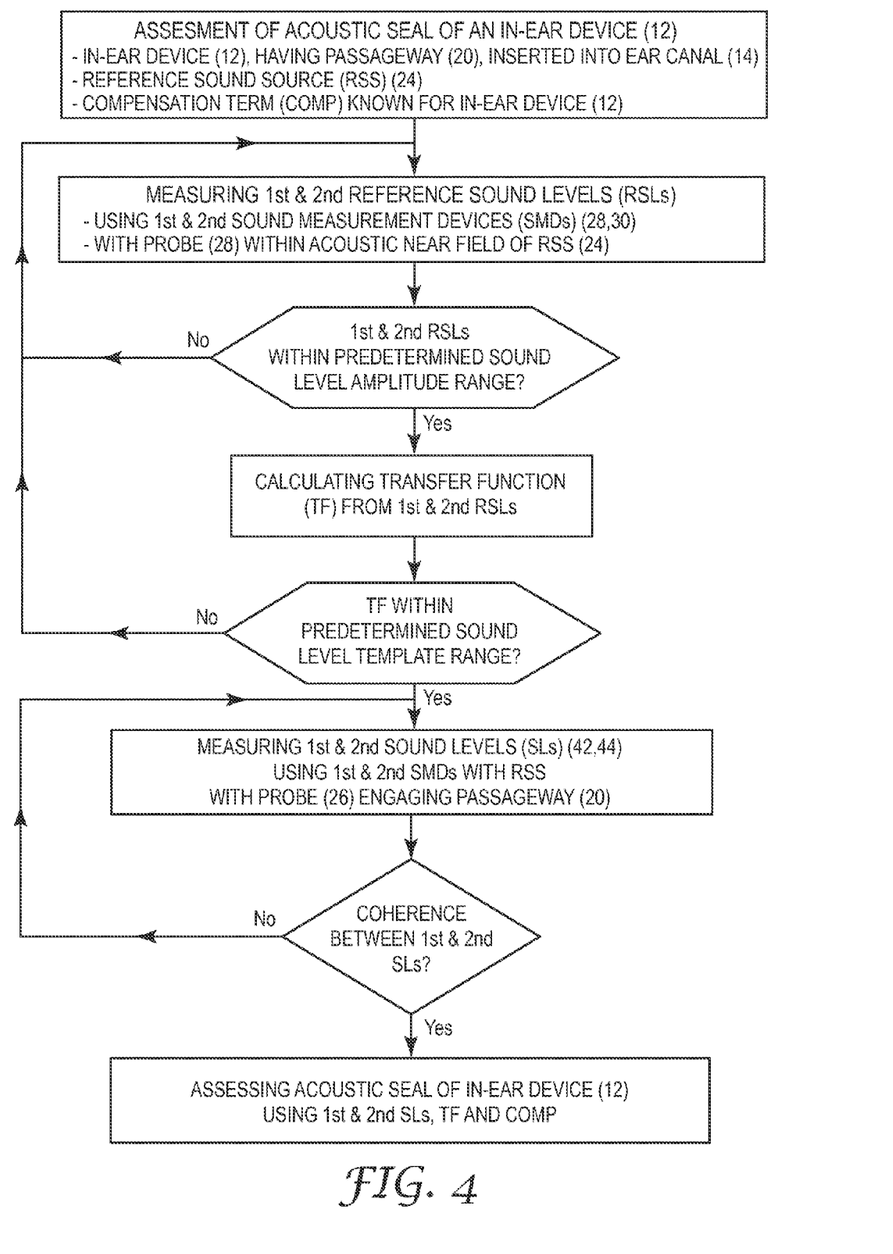
FIG. 4 is a simplified flow diagram of a method for assessing in-situ an acoustic seal of an in-ear device in accordance with an embodiment of the present invention.

More specifically, the present invention teaches a method for assessing in-situ an acoustic seal of an in-ear device 12 using an apparatus 10 having a sound measurement device 28 connected thereto, as shown in the simplified flow diagram of FIG. 4 in which all steps, including optional ones, are illustrated. The method comprises:

a) calibrating the sound measurement device 28 by measuring a reference sound level with the sound measurement device 28 when being submitted to a sound source 24 and when being located in a close relationship relative thereto;

b) measuring a first sound level outside the ear canal 14 with the sound measurement device 28 when submitted to the sound source 24 and when located in a close relationship relative to the in-ear device 12 and outside the ear canal 14;

c) measuring a second sound level inside the ear canal 14 with the sound measurement device 28 when submitted to the sound source 24 and when engaged into and occluding the passageway 20 with the in-ear device 12 inserted inside the ear canal 14; and d) assessing the acoustic seal of the in-ear device 12 by subtracting said second sound level from said first sound level.

The method further includes:

a1) assessing validity of said reference sound level by determining that the reference sound level is within a predetermined sound level amplitude range, if not step a) is repeated.

Typically, steps b) and c) are simultaneously performed using first 28 and second 30 sound measurement devices, respectively, preferably using the dual microphone probe 26 or the like. Accordingly, step a) includes calibrating first and second sound measurement devices by measuring first and second reference sound levels with the dual probe 26 when being submitted to a reference sound source and when being located in a close relationship or in an acoustic near field relative thereto. Step a) further includes determining a transfer function between the first and second reference sound levels.

Then, step a1) further includes assessing validity of the first and second reference sound levels by determining that the transfer function is within a predetermined sound level template range.

Step d) further includes indicating presence of acoustic seal when attenuation between the first and second sound levels is equal to or larger than a predetermined threshold value within a predetermined frequency range. As an example, the predetermined threshold value could be 11 dB (the NR, ANSI S3.19 test, within the 98% percentile) at about 250 Hz.

Typically, steps b) and c) are also simultaneously performed using first 28 and second 30 sound measurement devices, respectively. And step d) includes:

d1) assessing validity of the first and second sound levels by determining coherence there between preferably within a predetermined frequency range, if not steps b) and c) are repeated.

Determining coherence between the first 42 and second 44 sound levels includes determining that the second sound level 44 substantially linearly follows a contour of the first sound level 42, as schematically depicted in FIG. 1. For example, if the user happens to talk, cough or even swallow during the measurement of the second sound level 44, the latter would show acoustic noise induced by the user's voice, thereby not linearly following the contour of the first sound level 42, leading to a non-coherence between the two.

Furthermore, step d) includes assessing the acoustic seal of the in-ear device 12 by subtracting the second sound level 44 from said first sound level 42 and using the transfer function.

As described hereinabove, the assessment of the acoustic seal of the in-ear device 12 further includes using a compensation term (COMP) that relates to the type of in-ear device 12.

The calibration is typically performed before each test to ensure proper functioning of the dual probe 26 as well as the real-time reassessment of the transfer function thereof for accurate measurements.

The above detailed acoustic seal test ensures that the in-ear device 12 or earplug fits properly inside the ear canal 14 of the user, thereby providing a good acoustic seal.

A stability and reliability test that simply monitors the coherence of the transfer function (between external 28 and internal 30 microphones) in the 125 Hz octave band for example is easily performed by the apparatus 10 using the above method.

Figure 5:
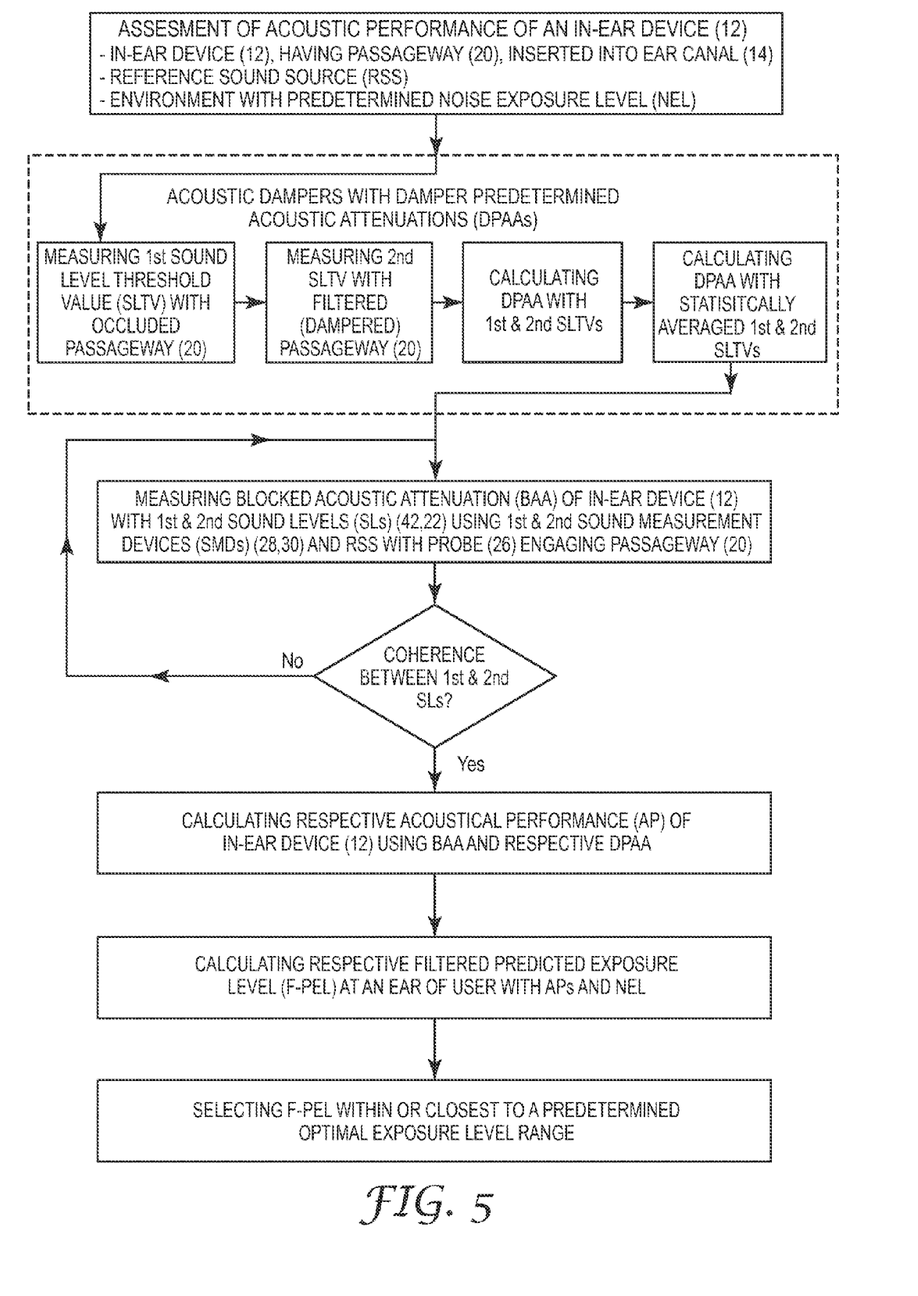
FIG. 5 is a simplified flow diagram of an embodiment of a method for assessing an acoustical performance of an in-ear device according to the present invention.

A similar method for assessing an acoustical performance of an in-ear device 12 using an apparatus 10 is shown in the simplified flow diagram of FIG. 5 in which all steps, including optional ones, are illustrated. The passageway 20 of the in-ear device 12 is typically adapted to receive an acoustic damper 46 therein, preferably inside a predetermined section or chamber 47 thereof having an enlarged diameter or the like. The acoustic damper 46 typically has a predetermined acoustic attenuation thereof. The method comprises:

a) calculating an acoustical performance of the in-ear device 12 with the acoustical damper 46 inserted in the passageway 20 thereof from a measured blocked acoustic attenuation obtained with the passageway 20 being occluded using a sound measurement device 30 selectively engaged therein and the predetermined damper acoustic attenuation.

Typically, the method further includes, before step a), the step of:

measuring a blocked acoustic attenuation of the in-ear device 12 with the passageway 20 being occluded using the sound measurement device 30 being selectively and alternately engaged therein and disengaged therefrom (or using a second sound measurement device 28 in the environment).

The predetermined damper acoustic attenuation is typically obtained through the following steps:

submitting a user wearing the in-ear device 12 with the passageway 20 thereof being occluded to a gradually increasing or decreasing a volume of a sound level of a predetermined frequency range to determine a first sound level threshold value at which the user start or stop hearing the sound;

submitting a user wearing the in-ear device 12 with the acoustic damper 46 inserted in the passageway 20 thereof to a gradually increasing or decreasing a volume of a sound level of a predetermined frequency range to determine a second sound level threshold value at which the user start or stop hearing the sound; and calculating the predetermined damper acoustic attenuation from a difference between the first and second sound level threshold values or preferably, from a difference between first and second average sound level thresholds obtained from a statistically significant number of the first and second sound level threshold values, respectively.

Alternatively, the predetermined damper acoustic attenuation may be typically obtained through the same steps with reference to first and second sound threshold values determined with a gradually increasing or decreasing a frequency of a sound level of a predetermined volume range at which the user stop or start hearing the sound.

As the in-ear device 12 is typically for being worn by a user subjected to an environment with a predetermined noise exposure level, the method further includes:

b) calculating a filtered exposure level at an ear of the user would be subjected to when protected by the in-ear device 12 with the acoustic damper 46 inserted in the passageway 20 thereof inside the environment from the calculated acoustical performance and the predetermined sound exposure level.

Since a plurality of acoustic dampers 48, each having a respective predetermined damper acoustic attenuation thereof, may be considered, the method would, after calculating respective filtered exposure levels with the different dampers 48, further includes:

c) selecting one of the plurality of acoustic dampers 48 providing a corresponding filtered exposure level within or closest to a predetermined optimal exposure level range, typically between about 75 dBA and about 80 dBA.

Similarly, an exposure level range between about 70 dBA and about 75 dBA or between about 80 dBA and about 85 dBA would be considered acceptable. An exposure level above 85 dBA would be considered unacceptably insufficient and dangerous to the user for over exposure, while an exposure level below 70 dBA would be unacceptably overprotecting and also dangerous because speech and warning signals would essentially not be heard by the user.

To be more practical, similarly to the quasi-subjective evaluation of the REAT made to get the compensation term COMP and the PAR, an evaluation of the attenuation of an in-ear device in a full-block configuration ($ATT_{Full-block}$) with the passageway occluded with a plug 50 or the like and in a filtered or "combo" configuration ($ATT_{combo}$) with predetermined acoustic dampers 48, such as plastic pieces of different densities or the like, occluding the passageway can be made to statistically assess the difference between the two configurations and therefore get the attenuation of the damper as follows:

$$ATT_{Damper} = -20 \log_{10}\left(10^{\frac{-ATT_{Combo}}{20}} - 10^{\frac{-ATT_{Full-block}}{20}}\right)$$

Figure 6:
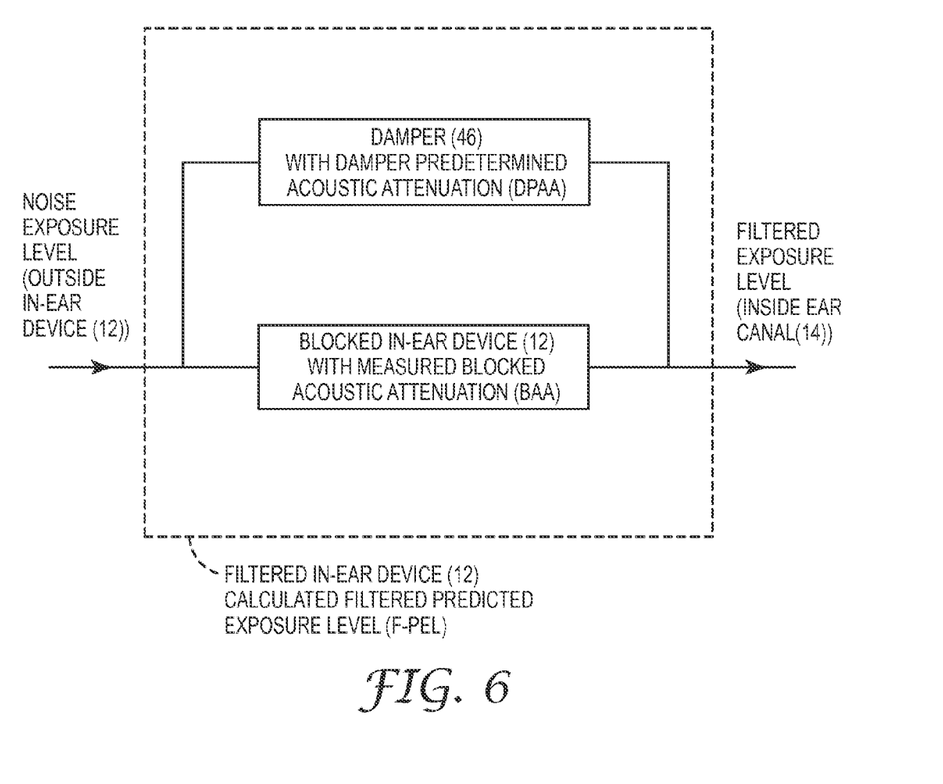
FIG. 6 is a simplified schematic block diagram illustrating the method of FIG. 5.

As shown in FIG. 6, the above-described prediction of an in-ear device attenuation filtered with acoustic dampers 48 is obtained from the an in-situ assessment of the acoustic seal performance of the device 12 and the knowledge of the attenuation of the dampers 48 illustrated above.

For the filter selection, once the earplug 12 has been tested successfully, an acoustical filter 46 can be placed into the inner bore 20 (since the microphone probe has been removed) to let more sound get through. The filters 48 are, but not limited to, pure acoustical dampers that are properly selected according to some guiding rules where the protected exposure level is computed from the estimated attenuation of the passive earplug 12 and the time weighted exposure level of the subject.

Such an acoustic protection test verifies what protection the earplug 12 offers and allows to adapt this amount of protection to match the user's needs, in terms of providing the filtered predicted exposure level (F-PEL) of the individual with the earplug 12 when subjected to the specific noise environment.

Figure 7:
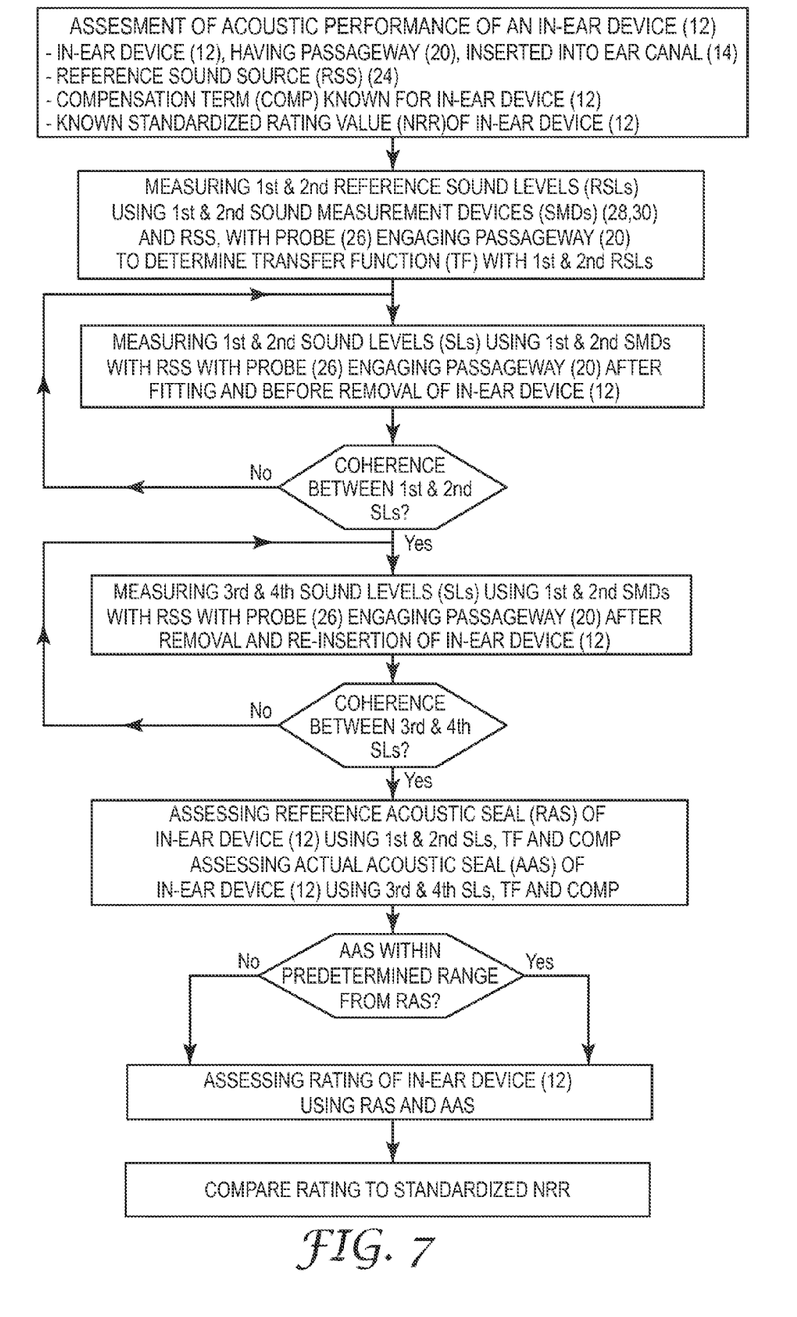
FIG. 7 is a simplified flow diagram of another embodiment of a method for assessing an acoustical performance of an in-ear device according to the present invention.

The present invention further refers to a method for assessing an acoustical performance of an in-ear device 12 using an apparatus 10, as shown in the simplified flow diagram of FIG. 7 in which all steps, including optional ones, are illustrated. The method comprises:
a) measuring a first sound level outside the ear canal 14 with the sound measurement device 28 when submitted to the sound source 24 and when located in a close relationship relative to the in-ear device 12 and outside the ear canal 14;
b) measuring a second sound level inside the ear canal 14 with the sound measurement device 28 when submitted to the sound source 24 and when engaged into and occluding the passageway 20 with the in-ear device 12 inserted inside the ear canal 14 after being fitted thereto and before removal therefrom;
c) measuring a third sound level inside the ear canal 14 with the sound measurement device 28 when submitted to the sound source 24 and when engaged into and occluding the passageway 20 with the in-ear device 12 inserted inside the ear canal 14 after removal therefrom and reinsertion therein by the wearer thereof;
d) assessing a reference acoustic seal of the in-ear device 12 by subtracting the second sound level from the first sound level and an actual acoustic seal of the in-ear device 12 by subtracting the third sound level from the first sound level; and
e) assessing a rating of the in-ear device 12 by comparing the actual acoustic seal relative to the reference acoustic seal.

Step d) includes indicating presence of acceptable acoustic seal when the actual acoustic seal is within a predetermined range from the reference acoustic seal, for example within about 3 dB.

Step e) typically further includes comparing the obtained rating to a standardized rating value (NRR) corresponding to a type of the in-ear device 12.

When using the dual microphone probe 26, steps a) and b) are simultaneously performed using first 28 and second 30 sound measurement devices, respectively. Then step c) includes measuring a third sound level inside the ear canal 14 with the second sound measurement device 30 when submitted to the sound source 24 and when engaged into and occluding the passageway 20 with the in-ear device 12 inserted inside the ear canal 14 after removal therefrom and reinsertion therein by the wearer thereof, and measuring a fourth sound level outside the ear canal 14 with the first measurement device 28 when submitted to the sound source 24 and when located in a close relationship relative to the in-ear device 12 and outside the ear canal 12. The reference acoustic seal of the in-ear device 12 is assessed by subtracting the second sound level from the first sound level, and the actual acoustic seal of the in-ear device 12 by subtracting the third sound level from the fourth sound level.

Typically, the method includes, before step a), the step of:
simultaneously measuring first and second reference sound levels with the first and second sound measurement devices 28, 30, respectively, when being submitted to a reference sound source 24 and when being in an acoustic near field relative thereto, and determining a transfer function between the first and second reference sound levels.

Then, assessment of the reference acoustic seal of the in-ear device 12 is made by subtracting the second sound level from the first sound level and using the compensation term (COMP) and the transfer function, and the actual acoustic seal of the in-ear device 12 is made by subtracting the third sound level from the fourth sound level and using the compensation term and the transfer function.

A quick re-insertion test, corresponding to the post-curing sound level measurements minus the subject-fit P-PAR measurements, is also performed by the present apparatus 10 in order to assess the quality of the reinsertion of an in-ear device 12 from objective measurements before removal of the fitted device 12 and after re-insertion thereof by the user himself.

The above rating test of the apparatus 10 ensures that the earplug 12 offers at least the corresponding published NRR; thereby ensuring that the earplug 12 does not need to be derated (typically by a factor of two for earplugs, according to Occupational Safety and Health Association (OSHA) to account for discrepancies between in-field performance and laboratory certification measurement tests). For example, if the P-PAR (at 84% confidence level) is larger than the published NRR (about 17 dB for example), then the user belongs to the 98% percentile category of people having standard minimal required hearing protection and therefore not subjected to any derating rule factor.

Alternatives

As shown in FIG. 1, a simple apparatus 10 of the present invention could be used to quickly perform on-site in-situ acoustic seal performance test of in-ear devices 12 with simple handheld devices with simple user interface 32 as controllers 22' instead of more versatile computers 22 that could allow to perform multiple different tests and measurements for different in-ear devices 12 with known normalized data stored therein.

Although the present method and apparatus for objective assessment of in-ear device acoustical performance have been described with a certain degree of particularity, it is to be understood that the disclosure has been made by way of example only and that the present invention is not limited to the features of the embodiments described and illustrated herein, but includes all variations and modifications within the scope and spirit of the invention as hereinafter claimed.

The invention claimed is:

1. An apparatus for assessing in-situ an acoustic seal of an in-ear device, the in-ear device having a passageway extending therethrough, the passageway being in fluid communication with an ear canal of an ear when the in-ear device is inserted therein, said apparatus comprising:
   a controller unit operatively connectable to a sound source;
   a sound measurement device operatively connecting to said controller unit, said sound measurement device being selectively locatable in a close relationship relative to the in-ear device and outside the ear canal for measuring a first sound level outside the ear canal when submitted to the sound source, said sound measurement device being removably engageable into the passageway to selectively occlude the passageway for measuring a second sound level inside the ear canal with the in-ear device inserted therein when submitted to the sound source; and
   a supporting device for releasably supporting said sound measurement device located in a close relationship relative to the sound source for measuring a reference sound level when being submitted thereto, wherein the supporting device is mountable on the sound source, releasably supporting the sound measurement device thereon.

2. The apparatus of claim 1, wherein said supporting device is a resilient clip mountable on the sound source, said clip releasably and resiliently holding said sound measurement device.

3. The apparatus of claim 1, wherein said controller unit controls operation of the sound source.

4. The apparatus of claim 1, wherein said controller unit includes the sound source.

5. The apparatus of claim 1, further including a user interface unit operatively connecting to said controller unit.

6. The apparatus of claim 5, wherein said controller unit analyzes said reference sound level and assesses calibration of said sound measurement device, said controller unit communicating with said user interface unit to indicate to the user proper functioning of said sound measurement device.

7. The apparatus of claim 5, wherein said controller unit assesses an acoustic seal of the in-ear device by comparing said first and second sound levels to one another, said controller unit further assessing an acoustic seal by further using a compensation term relating to the in-ear device, said controller unit communicating with said user interface unit to indicate to the user proper acoustic seal of the in-ear device inside the ear.

8. The apparatus of claim 5, wherein said user interface unit includes at least one of a keypad, a keyboard, an alpha-numerical display, a speaker, a led-type display, a monitor-type display, a socket-type connection port and a wireless type connection port.

9. The apparatus of claim 1, wherein said sound measurement device is a first sound measurement device, said apparatus further including a second sound measurement device operatively connecting to said controller device, said first sound measurement device being selectively locatable in a close relationship relative to the in-ear device and outside the ear canal for measuring the first sound level outside the ear canal when submitted to the sound source, said second sound measurement device being removably engageable into the passageway to selectively occlude the passageway for measuring the second sound level inside the ear canal with the in-ear device inserted therein when submitted to the sound source.

10. The apparatus of claim 9, wherein said means for releasably supporting said sound measurement device releasably supports said first and second sound measurement devices located in a close relationship relative to the sound source for measuring first and second reference sound levels when being submitted thereto, relatively.

11. The apparatus of claim 10, wherein said first and second sound measurement devices are connected to one another.

12. The apparatus of claim 11, wherein said first and second sound measurement devices are connected in a back-to-back relationship relative to one another.

13. The apparatus of claim 11, wherein said first and second sound measurement devices form a dual microphone probe.

14. The apparatus of claim 10, further including a user interface unit operatively connecting to said controller unit.

15. The apparatus of claim 14, wherein said controller unit analyzes said first and second reference sound levels and assesses calibration of said first and second sound measurement devices, said controller unit communicating with said user interface unit to indicate to the user proper functioning of said first and second sound measurement devices.

16. The apparatus of claim 14, wherein said controller unit analyzes said first and second sound levels and assesses validity of said first and second sound levels, said controller unit communicating with said user interface unit to indicate to the user proper measurements of said first and second sound levels.

17. The apparatus of claim 16, wherein said controller unit further assesses an acoustic seal of the in-ear device by comparing said first and second sound levels to one another, said controller unit communicating with said user interface unit to indicate to the user proper acoustic seal of the in-ear device inside the ear.

18. The apparatus of claim 16, wherein said controller unit further assesses an acoustic seal of the in-ear device by comparing said first and second sound levels to one another and by using a transfer function determined from said first and second reference sound levels, said controller unit communicating with said user interface unit to indicate to the user proper acoustic seal of the in-ear device inside the ear.

19. The apparatus of claim 18, wherein said controller unit further assesses an acoustic seal by further using a compensation term relating to the in-ear device.

20. The apparatus of claim 14, wherein said user interface unit includes at least one of a keypad, a keyboard, an alpha-numerical display, a speaker, a led-type display, a monitor-type display, a socket-type connection port and a wireless-type connection port.

* * * * *